(12) United States Patent
Herr et al.

(10) Patent No.: US 6,506,739 B1
(45) Date of Patent: Jan. 14, 2003

(54) BIS-(N,N'-BIS-(2-HALOETHYL)AMINO) PHOSPHORAMIDATES AS ANTITUMOR AGENTS

(75) Inventors: R. Jason Herr, Voorheesville, NY (US); Robert T. Lum, Palo Alto, CA (US); Steven R. Schow, Redwood Shores, CA (US); Fanying Meng, San Francisco, CA (US); Michael R. Kozlowski, Poway, CA (US); Pavel Zhichkin, Albany, NY (US)

(73) Assignee: Telik, Inc., South San Francisco, CA (US)

( * ) Notice: Subject to any disclaimer, the term of this patent is extended or adjusted under 35 U.S.C. 154(b) by 0 days.

(21) Appl. No.: 09/847,533

(22) Filed: May 1, 2001

(51) Int. Cl.[7] ................ A61K 31/664; C07F 9/24; A61P 35/04
(52) U.S. Cl. ............... 514/140; 514/141; 558/170; 558/171; 558/177; 558/178; 558/195
(58) Field of Search .................. 558/170, 171, 558/177, 178, 195; 514/140, 141

(56) References Cited

U.S. PATENT DOCUMENTS

| | | | |
|---|---|---|---|
| 4,734,225 A | 3/1988 | Eibl | 260/386 |
| 5,190,929 A | 3/1993 | Borch et al. | 514/80 |
| 5,306,727 A | 4/1994 | Borch et al. | 514/398 |
| 5,556,942 A | 9/1996 | Kauvar et al. | 9/199 |
| 5,622,936 A | 4/1997 | Wiessler et al. | 514/25 |

FOREIGN PATENT DOCUMENTS

| | | |
|---|---|---|
| DE | 32 39 858 A1 | 1/1984 |
| DE | 38 35 772 A1 | 4/1990 |
| DE | 195 24 515 A1 | 1/1997 |
| EP | 0 072 531 | 2/1983 |
| GB | 2 207 674 A | 2/1989 |
| WO | WO 95/09866 | 4/1995 |

OTHER PUBLICATIONS

Herr, et al, May 2001, Organic Process Research and Development, 5, 442–444.*

Kröger H. et al., "Wirkung carcinostatischer Verbindungen auf die Konzentration von Diphosphopridin–nucleotid in Tumoren", Arneimittel Forschung Drug Research, vol. 9, No. 10, 1959, pp. 598–600.

Arnold H. et al, "über Beziehungen zwischen chemischer konstitution und cancerotoxischer Wirkung in der Reihe der Phosphamidester des Bis–(beta–chloräthyl)–amins", Arzneimittel Forschung, Drug Research, vol. 11, No. 2a, 1961, pp 144–158.

Akira Takamizawa, et al., "Synthesis of 4–Hydroperoxy–1, 3,2–diazaphosphorinane–2–oxides related to the Activated Cyclophosphamide", Chemical and Pharmaceutical Bulletin, vol. 26, No. 3, 1978, pp. 790–797.

\* cited by examiner

*Primary Examiner*—Ceila Chang
*Assistant Examiner*—Andrea D. Small
(74) *Attorney, Agent, or Firm*—Heller Ehrman White & McAuliffe LLP

(57) ABSTRACT

Bis-(N,N'-bis-(2-haloethyl)amino)phosphoramidates, pharmaceutical compositions containing them, methods of treatment using them, and processes for their preparation. The compounds possess anti-tumor activities or are capable of being modified to have anti-tumor activities; and this invention relates to the use of the compounds in methods for the treatment of tumors and, especially, for the treatment of cancer.

20 Claims, No Drawings

BIS-(N,N'-BIS-(2-HALOETHYL)AMINO) PHOSPHORAMIDATES AS ANTITUMOR AGENTS

CROSS-REFERENCE TO RELATED APPLICATION

This application is related to (U.S. application Ser. No. 09/563,181, filed May 2, 2000.

BACKGROUND OF THE INVENTION

1. Field of the Invention

This invention relates to bis-(N,N'-bis-(2-haloethyl)amino)phosphoramidates, pharmaceutical compositions containing them, methods of treatment using them, and processes for their preparation. The compounds possess anti-tumor activities or are capable of being modified to have anti-tumor activities; and this invention relates to the use of the compounds in methods for the treatment of tumors and, especially, for the treatment of cancer.

2. Description of Related Art

Current cancer chemotherapy protocols involve administration to patients of anti-mitotic drugs such as adriamycin, vincristine, cisplatin, doxorubicin, daunomycin and methotrexate, toxins such as diphtheria toxin, pseudomonas toxin and ricin, and anti-tumor drugs such as cyclophosphamide and isophosphamide. Cyclophosphamide is one of the most widely used anti-cancer agents in the world and is administered in combination with a number of other drugs to treat a wide variety of hematologic and solid tumors. However, several features of the cyclophosphamide detract from its clinical efficacy. For example, the drug requires metabolic activation in the liver to produce metabolites that are toxic to cancer cells. The drug is specifically toxic to the urinary bladder, and it also displays the bone marrow toxicity typical of the alkylating agent class of anti-cancer drugs. Cyclophosphamide is a potent suppressor of the immune system at the doses used to treat cancer, thus decreasing the infection-fighting ability of patients already debilitated by their disease. Finally, repeated use of cyclophosphamide frequently results in the development of resistance to the drug in a patient's cancer cells, thus rendering the drug ineffective.

Phosphoramidate derivatives have long been known in the literature and are well documented as alkylating reagents. Some of them have been found to be useful in the treatment of cancer (for a review see, DeVita, "Principles of Cancer Therapy", pages 765–788 in Petersdorf, et al. Principles of Internal Medicine, $10^{th}$ ed. McGraw-Hill, NY., 1983). Cyclophospharnide analogs are also well known to the literature and have been extensively derivatized (Cyclophosphamide, Merck Index, $11^{th}$ Edition pages 429–430, U.S. Pat. No. 5,190,929). However, there have been relatively few references to bis-(N,N'-bis-(2-chloroethyl)amino) phosphoramidates (DE19524515, U.S. Pat. No. 5,306,727, WO9306120, DE3835772, GB2207674, DE3239858, EP072531). U.S. Pat. No. 5,556,942 discloses the compound

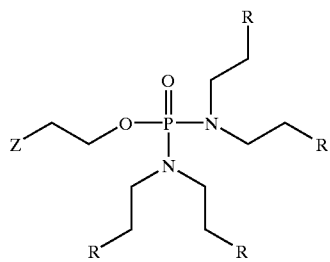

in which Z is bromine, and R is hydrogen, or R is chlorine as a synthetic reaction intermediate.

SUMMARY OF THE INVENTION

In a first aspect, this invention is phosphoramidate compounds of the formula:

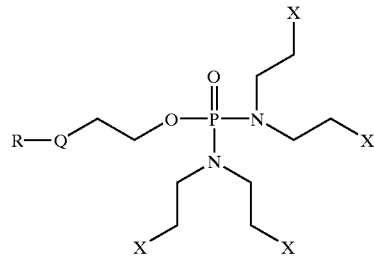

where:
- X is a halogen atom;
- Q is O, S, or NH; and
- R is hydrogen, lower alkyl, substituted lower alkyl, aryl, substituted aryl, heteroaryl, or substituted heteroaryl, or is R'CO—, R'NHCO—, R'SO$_2$—, or R'NHSO$_2$— where R' is hydrogen, lower alkyl, substituted lower alkyl, aryl, substituted aryl, heteroaryl, or substituted heteroaryl; or R-Q together is chlorine, and the pharmaceutically acceptable salts thereof.

In a second aspect, this invention is pharmaceutical compositions comprising a therapeutically effective amount of a compound of the first aspect of the invention and at least one pharmaceutically acceptable carrier.

In a third aspect, this invention is methods of treatment of disease states in a mammal where administration of an anti-mitotic agent is beneficial, such as tumors and cancer, the method comprising to the mammal a therapeutically effective amount of a compound of the first aspect of the invention, in particular as a composition of the second aspect of the invention.

In a fourth aspect, this invention is processes for the preparation of compounds of the first aspect of the invention.

DETAILED DESCRIPTION OF THE INVENTION

Definitions

Terms used herein are based upon their recognized meanings and should be clearly understood by those skilled in the art.

The term "halogen" or "halo" includes fluorine, chlorine, bromine, and iodine. Preferred halogens are chlorine and bromine.

The term "alkyl", as in "alkyl" or "alkyloxy", means a $C_1$–$C_{20}$ monovalent hydrocarbyl group which may be linear, branched, or cyclic. The term "lower alkyl", as in "lower alkyl", "halo-lower alkyl", "aryl(lower)alkyl", or "heteroaryl(lower)alkyl", means a fully saturated monovalent hydrocarbon group having from 1 to 10 carbon atoms containing only carbon and hydrogen atoms, and which may be cyclic, branched or straight chain. This term is exemplified by groups such as methyl, ethyl, isopropyl, propyl, butyl, isobutyl, sec-butyl, tert-butyl, pentyl, hexyl, cyclopentyl, cyclopropylmethyl, cyclohexyl or cyclohexylmethyl. In the context of the present invention, a lower alkyl of 1 to 6 carbon atoms is preferred.

The term "substituted alkyl or substituted lower alkyl" is an alkyl or lower alkyl, respectively, which is mono-, di-, or trisubstituted with a group selected from aryl, $R^1$-substituted aryl, heteroaryl, nitro, cyano, halogen, —$OR^1$, —$SR^1$, —$C(O)R^1$, —$OC(O)R^1$, —$C(O)OR^1$, —$NR^1{}_2$, —$SO_2OR^1$, —$OSO_2R^1$, —$SO_2NR^1{}_2$, —$NR^1SO_2R^1$, —$CONR^1{}_2$, or —$NR^1C(O)R^1$, where each $R^1$ is, independently, hydrogen, lower alkyl, $R^2$-substituted lower alkyl, aryl, $R^2$-substituted aryl, heteroaryl, heteroaryl(lower)alkyl, $R^2$-substituted aryl (lower)alkyl, or aryl(lower)alkyl and each $R^2$ is, independently, hydroxy, halogen, lower alkyloxy, cyano, thio, nitro, lower alkyl, halo-lower alkyl or amino. Substituted alkyls or substituted lower alkyls which are substituted with one to three of the substituents selected from the group consisting of cyano, halo, lower alkyloxy, thio, nitro, amino, and hydroxy are particularly preferred.

The term "halo-lower alkyl" means a lower alkyl substituted with one to three halo groups, such as —$CF_3$, —$CH_2CF_3$ and —$CH_2CCl_3$.

The term "aryl(lower)alkyl" means a lower alkyl which is substituted with an aryl. A "substituted aryl(lower)alkyl" means an aryl(lower)alkyl having one to three substituents on the aryl portion or the alkyl portion of the radical, or both.

The term "heteroaryl(lower)alkyl" means a lower alkyl which is substituted with a heteroaryl. A "substituted heteroaryl(lower)aryl" means a heteroaryl(lower)alkyl having one to three substituents on the heteroaryl portion or the alkyl portion of the radical, or both.

The term "lower alkyloxy" means an —$OR^3$ radical, where $R^3$ is a lower alkyl.

The term "aryl", as in "aryl", "aryloxy", and "aryl(lower)alkyl", means a monovalent group derived from an aromatic hydrocarbon containing 6 to 20 ring carbon atoms, having a single ring (e.g., phenyl), or two or more condensed rings, preferably 2 to 3 condensed rings (e.g., naphthyl), or two or more aromatic rings, preferably 2 to 3 aromatic rings, which are linked by a single bond (e.g., biphenyl). The aryl is preferably $C_6$–$C_{16}$ and even more preferably, $C_6$ to $C_{14}$.

The term "substituted aryl" means an aryl substituted with one to three substituents selected from alkyl, substituted alkyl, halogen, cyano, nitro, —$SR^1$, —$OR^1$, —$C(O)R^1$, —$OC(O)R^1$, —$SO_2OR^1$, —$OSO_2R^1$, —$SO_2NR^1{}_2$, —$NR^1SO_2R^1$, —$C(O)OR^1$, —$NR^1{}_2$, —$CONR^1{}_2$, or —$NR^1C(O)R^1$, where each $R^1$ is, independently, hydrogen, lower alkyl, $R^2$-substituted lower alkyl, aryl, $R^2$-substituted aryl, heteroaryl, heteroaryl(lower)alkyl, aryl(lower)alkyl, or $R^2$-substituted aryl(lower)alkyl and each $R^2$ is, independently, hydroxy, halo, lower alkyloxy, cyano, thio, nitro, lower alkyl, halo-lower alkyl or amino. In addition, any two adjacent substituents on the aryl may optionally together form a lower alkylenedioxy. Particularly preferred substituents on the substituted aryl include hydroxy, halo, lower alkyloxy, cyano, thio, nitro, lower alkyl, halo-lower akyl, halo-lower alkyl, or amino.

The term "heteroaryl", as in heteroaryl and heteroaryl (lower)alkyl, means a radical derived from an aromatic hydrocarbon containing 5 to 14 ring atoms, 1 to 5 of which are hetero atoms chosen, independently, from N, O, or S, and includes monocyclic, condensed heterocyclic, and condensed carbocyclic and heterocyclic aromatic rings (e.g., thienyl, furyl, pyrrolyl, pyrimidinyl, isoxazolyl, oxazolyl, indolyl, isobenzofuranyl, purinyl, isoquinolyl, pteridinyl, imidazolyl, pyridyl, pyrazolyl, pyrazinyl, quinolyl, etc.).

The term "substituted heteroaryl" means a heteroaryl having from one to three substituents selected from alkyl, $R^1$-substituted alkyl, halo, cyano, nitro, —$SR^1$, —$OR^1$, —$C(O)R^1$, —$OC(O)R^1$, —$SO_2OR^1$, —$OSO_2R^1$, —$SO_2NR^1{}_2$, —$NR^1SO_2R^1$, —$C(O)OR^1$, —$NR^1{}_2$, —$CONR^1{}_2$, or —$NR^1C(O)R^1$, where each $R^1$ is independently hydrogen, lower alkyl, $R^2$-substituted lower alkyl, aryl, $R^2$-substituted aryl, heteroaryl, heteroaryl(lower)alkyl, aryl(lower)alkyl, or $R^2$-substituted aryl(lower)alkyl and each $R^2$ is, independently, hydroxy, halo, lower alkyloxy, cyano, thio, nitro, lower alkyl, halo-lower alkyl, or amino. In addition, any two adjacent substituents on the heteroaryl may optionally together form a lower alkylenedioxy. Particularly preferred substituents on the substituted heteroaryl include hydroxy, halo, lower alkyloxy, cyano, thio, nitro, lower alkyl, halo-lower alkyl, halo-lower alkyl, or amino.

The term "disease", in the context of the present invention, is intended to include tumors, in particular cancer, and other diseases which may benefit from an anti-mitotic agent including but not limited to benign hyperplasia and infections by pathogenic agents such as fungal and parasitic infections.

The term "pharmaceutically acceptable salts" means salts which may be formed when acidic groups, more specifically, acidic protons present are capable of reacting with inorganic or organic bases. Acidic protons are, for example, present in the groups —$OR^1$, —$SO_2OR^1$, or —$C(O)OR^1$. Typically the parent compound is treated with an excess of an alkaline reagent, such as hydroxide, carbonate or alkoxide, containing an appropriate cation. Cations such as $Na^+$, $K^+$, $Ca^{2+}$ and $NH_4{}^+$ are examples of cations present in pharmaceutically acceptable salts. The $Na^+$ salts are especially useful. Acceptable inorganic bases, therefore, include aluminum hydroxide, calcium hydroxide, potassium hydroxide, sodium carbonate and sodium hydroxide. Salts may also be prepared using organic bases, such as ethanolamine, diethanolamine, triethanolamine, N-methylglucamine, ethanolamine, and tromethamine. If the compounds of the invention contain a basic group, an acid addition salt may be prepared. Examples of basic groups are —$NR^1{}_2$ groups. Acid addition salts of the compounds are prepared in a standard manner in a suitable solvent from the parent compound and an excess of acid, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, hexanoic acid, heptanoic acid, cyclopentanepropionic acid, lactic acid, o-(4-hydroxy-benzoyl) benzoic acid, 1,2-ethanedisulfonic acid, 2-hydroxyethanesulfonic acid, benzenesulfonic acid, p-chlorobenzenesulfonic acid, 2-naphthalenesulfonic acid, camphorsulfonic acid, 4-methyl-bicyclo[2.2.2.]oct-2-ene-1-carboxylic acid, glucoheptonic acid, gluconic acid, 4,4'-methylenebis(3-hydroxy-2-naphthoic)acid, 3-phenylpropionic acid, trimethylacetic acid, tert-butylacetic acid, laurylsulfuric acid, glucuronic acid, glutamic acid, 3-hydroxy-2-naphthoic acid, stearic acid, muconic acid and the like. The term "pharmaceutically acceptable salts" also include inner salts or zwitterions. Zwitterions would be formed if a compound of Formula I contains both acidic protons and basic groups. "Inner salts" or "zwitterions" can be formed by transferring a proton from the carboxyl group onto the lone pair of electrons of the nitrogen atom in the amino group.

The term "stereoisomers" are compounds that have the same sequence of covalent bonds and differ in the relative disposition of their atoms in space.

The term "therapeutically effective amount" refers to the amount which, when administered to an animal for treating a disease, is sufficient to effect such treatment for the disease.

The term "anti-mitotic" refers to a drug or agent that interferes with the division of the nucleus of a eukaryotic cell.

The term "treating" or "treatment" of a disease in a mammal includes:

(1) preventing the disease from occurring in a mammal which may be predisposed to the disease but does not yet experience or display symptoms of the disease, (2) inhibiting the disease, i.e., arresting its development, or (3) relieving symptoms of the disease, i.e., causing regression of the disease.

Certain compounds of the invention may contain one or more chiral centers. In such cases, all stereoisomers also fall within the scope of this invention. The compounds within the scope of the invention therefore are understood to include the individually isolated stereoisomers as well as mixtures of such stereoisomers.

Preferred Embodiments

Within the compounds of the first embodiment of the invention, certain compounds (including as pharmaceutically acceptable salts of the compounds) are preferred.

These preferences include compounds where:

(1) X is chlorine or bromine, especially chlorine;

(2) Q is O;

(3) R is R'CO—, R'NHCO—, R'SO$_2$—, or R'NHSO$_2$—, where R' is hydrogen, lower alkyl, substituted lower alkyl, aryl, substituted aryl, heteroaryl, or substituted heteroaryl, especially where R is acetyl, benzoyl, benzenesulfonyl, para-bromobenzenesulfonyl, para-nitrobenzenesulfonyl, para-toluenesulfonyl, or methanesulfonyl; or (3') R is hydrogen, lower alkyl, substituted lower alkyl, aryl, substituted aryl, heteroaryl, or substituted heteroaryl; especially where R is hydrogen, methyl, or benzyl.

Within the compounds of the invention, compounds in which a given preference is met are preferred over those in which the preference is not met; and compounds having a greater number of preferences met are preferred over compounds in which a smaller number of preferences is met.

Particularly preferred compounds are those in which X is chlorine, Q is O, and R is hydrogen, benzyl, acetyl, benzoyl, benzenesulfonyl, para-bromobenzenesulfonyl, para-nitrobenzenesulfonyl, para-toluenesulfonyl, or methanesulfonyl, or R-Q together is chlorine; and the compounds 2-hydroxyethyl-N,N,N',N'-tetrakis(2-chloroethyl)phosphorodiamidate and 2-chloroethyl-N,N,N',N'-tetrakis(2-chloroethyl)phosphorodiamidate are particularly preferred.

Pharmacology and Utility

The compounds of Formula I possess anti-tumor activities or are capable of being modified to have anti-tumor activities. The 2-haloethyl, more specifically, the 2-chloroethyl portion of the molecule in these compounds can act directly as an alkylator of DNA or can be transformed into an aziridinyl. The aziridinyl form is a highly active form of the molecule and is the proposed mechanism for the nitrogen mustard class of compounds. Therefore, the compounds are effective in treating tumors and other diseases which may benefit from an anti-mitotic agent, such as benign hyperplasia and infections by pathogenic agents. These compounds do not have to be metabolically activated in the liver to acquire anti-tumor activity and, therefore, do not have the same toxicity profile as cyclophosphamides.

Administration and Pharmaceutical Compositions

The compounds of the invention may be administered in a therapeutically effective amount by any of the usual and acceptable routes to the patient being treated. Routes of administration include, but are not limited to, administration by injection, including intravenous, intraperitoneal, intramuscular, and subcutaneous injection, by transmucosal or transdermal delivery, through topical application, nasal spray, suppository and the like or may be administered orally.

The therapeutically effective amount may vary widely depending on the severity of the disease, the age and relative health of the patient, the potency of the compound used and other factors. It is usually in the range of approximately 1 milligram per Kg (mg/Kg) body weight per day to 1,000 mg/Kg body weight per day, preferably in the range of approximately 1 to 100 mg/Kg/day.

In general, compounds of the invention will be administered as pharmaceutical compositions which can take the form of tablets, pills, capsules, semisolids, powders, sustained release formulations, solutions, suspensions, elixirs, or any other appropriate composition and are comprised of, in general, a compound of formula I in combination with at least one pharmaceutically acceptable carrier. Acceptable carriers are non-toxic, aid administration, and do not adversely affect the therapeutic benefit of the compound of Formula I. Such excipient may be any solid, liquid or semisolid.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.) Preferred liquid carriers, particularly suitable for injection solutions, include water, saline, aqueous dextrose and glycols.

The amount of a compound of Formula I in the composition may vary widely depending upon the type of composition, size of a unit dosage, kind of excipients and other factors known to those skill in the art of pharmaceutical sciences. In general, the final composition will comprise from 1% w/w to 99% w/w, more preferably, 10% w/w to 90% w/w of the compound, most preferably 25% w/w to 75% w/w with the remainder being the excipient or excipients.

The pharmaceutical compositions are prepared following the conventional techniques of pharmacy.

Pharmaceutical compositions comprising a therapeutically effective amount of a compound of the first aspect of this invention (including as a pharmaceutically acceptable salt form of the compound), and at least one pharmaceutically acceptable carrier are likewise an embodiment of this invention.

The present invention further contemplates administration of a pharmaceutical composition of one or more compounds of the first aspect of this invention to be used alone or in combination with other pharmacological agents. A preferred embodiment of the present invention includes combination therapy where a pharmaceutical composition of one or more compounds of the first aspect of this invention are used in combination with other pharmacologically active agents selected from the group consisting of antibiotics, antineoplastic agents, tumoricidal agents, tumoristatic agents and the like. Such use of combination therapy may be readily practiced by those skilled in the art following generally accepted standards of medical care and based upon generally accepted clinical principles.

The present invention also contemplates methods of treatment for tumors, in particular cancer, in a mammal, comprising administering a therapeutically effective amount of a compound of the first aspect of this invention (including as a pharmaceutically acceptable salt form of the compound to a mammal in need thereof.

Synthesis of Compounds of Formula I

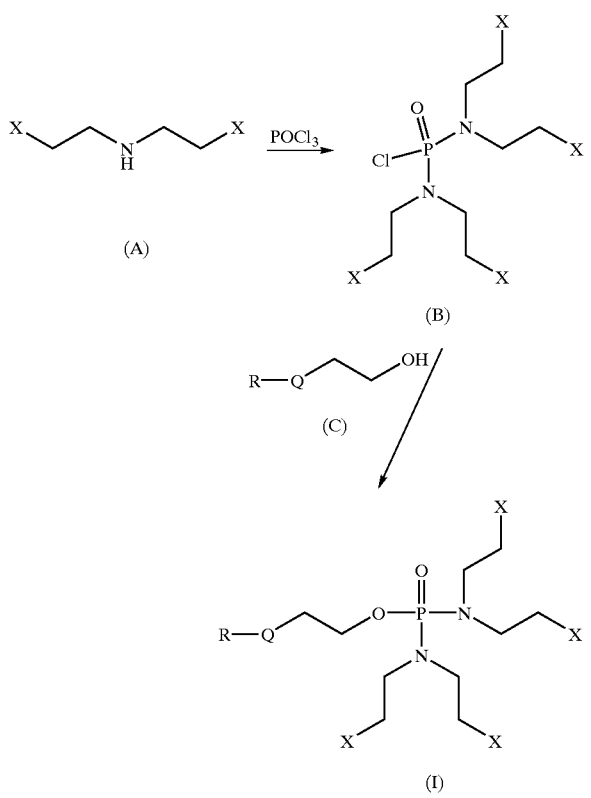

The compounds of Formula I may be prepared according to the reaction scheme depicted above and described below:

Compound B can be prepared by reacting phosphorus oxychloride with compound A, bis(2-haloethyl)amine halide. The reaction mixture is reacted in an inert solvent. Inert solvents may be aromatic hydrocarbons. A base is added to the reaction mixture, more preferably, an organic base such as organic amine, most preferably, triethylamine is added to the reaction mixture, and the reaction mixture is then stirred for an extended period of time at 0–50° C. The mixture, frequently a suspension, is heated to 0–100° C. and stirred for an extended period of time. The mixture is then cooled, treated with an adsorbent, for example, charcoal, stirred at room temperature, and filtered. The solvent is then removed to produce a compound B.

Compound B is subsequently reacted with a compound C. The reaction is carried out in a polar solvent. The reaction mixture is stirred/agitated and then cooled. Alkali alkoxide is added to the mixture, which is then slowly warmed to 0–50° C. and stirred for an extended period of time. A solution of hydrogen halide, for example, HCl, in water is introduced into the reaction mixture. The organic fraction is collected, and the aqueous fraction is extracted with a water-immiscible aprotic polar solvent (2×4 L). Water-immiscible aprotic polar solvents include dichloromethane, chloroform, and the like. The combined organic fractions are washed, and the solvents are removed under reduced pressure. The resulting crude product of the reaction, a compound of Formula (I), is then washed and purified by conventional means.

More specifically, compound 2 (see synthetic scheme 2, below) can be prepared by reacting phosphorous oxychloride with 1 namely, bis(2-haloethyl)amine hydrochloride. The reaction mixture in a solvent such as toluene, benzene, xylene and the like is stirred/agitated at a moderate rate (to provide a clear solution) and triethylamine is added to the reaction mixture over a period of 5–30 minutes. The reaction mixture is then stirred for an extended period of time at room temperature. To this mixture is added an additional amount of bis(2-haloethyl)amine hydrochloride and triethylamine. The resulting suspension is heated to the reflux temperature of the solvent and stirred for 16–24 hours. The mixture is then cooled to room temperature and treated with charcoal, stirred at room temperature for 2 hours and then vacuum filtered through a pad of Celite. The solvent is then removed under reduced pressure (30 mm Hg, final bath temperature at 50° C.) on a rotary evaporator to produce a compound 2.

Compound 2 thus prepared is then reacted with a compound 3. The reaction is carried out in a solvent such as tetrahydrofuran, dioxane, tert-butylmethylether and the like. The reaction mixture is stirred/agitated at a moderate rate (to provide a clear red solution) and the mixture is cooled to 0° C. using an ice/water bath. To this cooled solution is added potassium tert-butoxide (362 g, 3.22 moles) over 20 minutes. The reaction mixture is then slowly warmed to room temperature and stirred for an extended period of time (16–24 hours). A solution of hydrogen chloride in water is introduced into the reaction mixture at this stage. The organic fraction is collected and the aqueous fraction is extracted with ethyl acetate (2×4 L). The combined organic fractions are washed with saturated aqueous sodium chloride solution (1×4 L) and the solvents are removed under reduced pressure (30 mm Hg vacuum, final bath temperature at 50° C.) on a rotary evaporator. The resulting crude product of the reaction, a compound of Formula (I), is then washed and purified by conventional means.

In this synthesis, reactants such as phosphorus oxychloride, compounds 1 and 3 are all commercially available from sources such as Aldrich, Fluka and Alfa.

In the synthesis of certain compounds of Formula I, protective groups may be introduced and finally removed. Suitable protective groups for amino, hydroxyl, carboxyl groups are described in Greene, et al. "Protective Groups in Organic Synthesis," Second Edition, John Wiley and Sons, New York, 1991. Some derivatives require esterification of alcohols, which may be achieved by methods well known in the art (see, for example, Larock, "Comprehensive Organic Transformations", VCH Publishers, New York, 1989).

Accordingly, the process for preparing a compound of Formula I comprises one or more of the following steps:

(a) reacting a compound of Formula (2)

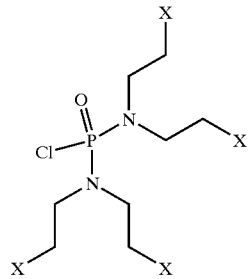
(2)

with a compound of Formula(3)

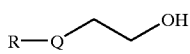
(3)

;or (b) elaborating substituents of a compound of Formula I in a manner known per se; or (c) converting a compound of Formula I where R is hydrogen and Q is oxygen into a compound of Formula I where R-Q together is an ester group; or (d) reacting the free base of a compound of Formula I with an acid to give a pharmaceutically acceptable addition salt; or (e) reacting an acid addition salt of a compound of Formula I with a base to form the corresponding free base; or (f) converting a salt of a compound of Formula I to another pharmaceutically acceptable salt of a compound of Formula I; or (g) resolving a racemic mixture of any proportions of a compound of Formula I to yield a stereoisomer thereof.

EXAMPLES

The following examples are given to enable those skilled in the art to more clearly understand and to practice the present invention. They should not be considered as limiting the scope of the invention, but merely as being illustrative and representative thereof.

In the synthetic examples, thin layer chromatography was performed using 1"×3" Analtech GF 350 silica gel plates with fluorescent indicator. Visualization of TLC plates was made by observation in iodine vapors. The proton and carbon magnetic resonance spectra were obtained on a Bruker AC 300 MHz Nuclear Magnetic Resonance spectrometer, using tetramethylsilane as an internal reference. Melting points were obtained using an electrothermal melting point apparatus and are uncorrected. Infrared spectra were obtained as KBr pellets and obtained on a Perkin-Elmer Spectrum 1000 FT-Infrared spectrophotometer. Mass spectroscopic analyses were performed on a Shimadzu QP-5000 GC/Mass Spectrometer (CI, methane) by direct injection. Thermal analyses were run on a Mettler Toledo DSC821e Differential Scanning Calorimeter.

Scheme 2
Synthesis of Compounds of Formula I

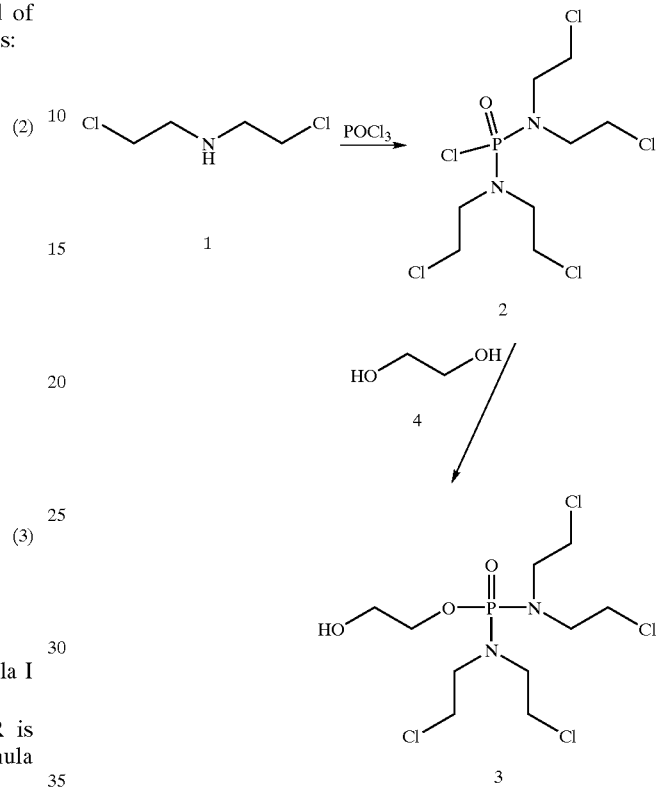

Example 1 Preparation of Compound 3 (Scheme 2)

Preparation of N,N,N',N'-Tetrakis(2-chloroethyl) phosphorodiamidic Chloride (2)

A 12-L, three-neck, round-bottom flask in an electric heating mantle was equipped with an overhead mechanical stirrer, a reflux condenser and a 2-L pressure-equalizing addition funnel capped with a nitrogen inlet/outlet bubbler. The flask was charged with phosphorous oxychloride (258 mL, 2.77 moles), bis(2-chloroethyl)amine hydrochloride (495 g, 2.77 moles), 1, and toluene (5 L). The stirrer was set to agitate at a moderate rate (to provide a clear solution) and triethylamine (812 mL, 5.82 moles) was added to the reaction mixture over 10 minutes. The reaction mixture was then stirred for 26 hours at room temperature. To this mixture was charged bis(2-chloroethyl)amine hydrochloride (505 g, 2.83 moles) and triethylamine (830 mL, 6.11 moles) over 10 minutes. The tan suspension was heated to toluene reflux (110° C.) and stirred for 22 hours. The mixture was then cooled to room temperature and treated with charcoal (500 g), stirred at room temperature for 2 hours and then vacuum filtered through a pad of Celite (1 kg). The solvent was removed under reduced pressure (30 mm Hg, final bath temperature 50° C.) on a rotary evaporator to produce N,N,N',N'-tetrakis(2-chloroethyl)phosphorodiamidic chloride, 2, as a reddish-brown oil (979 g, 97% yield). TLC analysis showed one spot ($R_f$=0.71; ethyl acetate:hexanes 1:1). The proton NMR spectrum was consistent with commercially available material.

Example 2

Preparation of 2-Hydroxyethyl-N,N,N',N'-tetrakis(2-chloroethyl)phosphorodiamidate (3)

A 12-L, three-neck, round-bottom flask was equipped with an overhead mechanical stirrer, a thermometer and a nitrogen inlet/outlet bubbler. The flask was charged with N,N,N',N'-tetrakis(2-chloroethyl)phosphorodiamidic chloride (979 g, 2.68 moles), 2, ethylene glycol (1.5 L, 26.8 moles), 4 and tetrahydrofuran (3 L). The stirrer was set to agitate at a moderate rate (to provide a clear red solution) and the mixture was cooled to 0° C. using an ice/water bath. To this cooled solution was added potassium tert-butoxide (362 g, 3.22 moles) over 20 minutes. The reaction mixture was then slowly warmed to room temperature and stirred for a total of 19 hours. A solution of hydrogen chloride in water (8 L, 1M) was introduced into the flask over 10 minutes. The organic fraction was collected and the aqueous fraction was extracted with ethyl acetate (2×4 L). The combined organic fractions were washed with saturated aqueous sodium chloride solution (1×4 L) and the solvents were removed under reduced pressure (30 mm Hg vacuum, final bath temperature at 50° C.) on a rotary evaporator to provide a dark reddish brown oil. This crude organic product was then dissolved with warm (40° C.) methyl tert-butyl ether (2 L) and allowed to cool to room temperature, stirring for a total of 14 hours. The resulting slurry was stirred for 30 minutes at 0° C. after which the precipitate was collected by vacuum filtration and washed with cold methyl tert-butyl ether (1 L). The combined filtrates were concentrated under reduced pressure (30 mmHg vacuum, final bath temperature at 50° C.) on a rotary evaporator to a volume of 500 mL and stirred for 30 minutes at 0° C. The resulting precipitate was collected by vacuum filtration and washed with cold methyl tert-butyl ether (200 mL). Two crops of solid product were then combined and dried overnight (30 mm Hg, 40° C.) to produce 2-hydroxyethyl-N,N,N',N'-tetrakis(2-chloroethyl) phosphorodiamidate, 3, as a tan powder (526 gm, 50% yield). TLC analysis showed one spot ($R_f$ 0.62; methanol:chloroform 1:9). Melting point: 76–78° C.; IR (KBr) 3372, 2957, 1459, 1344, 1206, 1098, 1053, 929 cm$^{-1}$; MS (CI, methane) m/z 391(MH$^+$), 353, 339, 248, 106. A thermal analysis (DSC) showed two exothermic decomposition ranges of 164–179 and 222–231 C.

The table shows compounds made by a similar method

| Compound | R-Q | X | MW |
|---|---|---|---|
| 5 | OH | Br | 568 |
| 6 | NH$_2$ | Cl | 389 |
| 7 | SH | Cl | 406 |
| 8 | Br | Cl | 453 |
| 9 | Cl | Cl | 408 |
| 10 | Br | Br | 631 |

Example 3

(Scheme 3)
Preparation of Compound 11

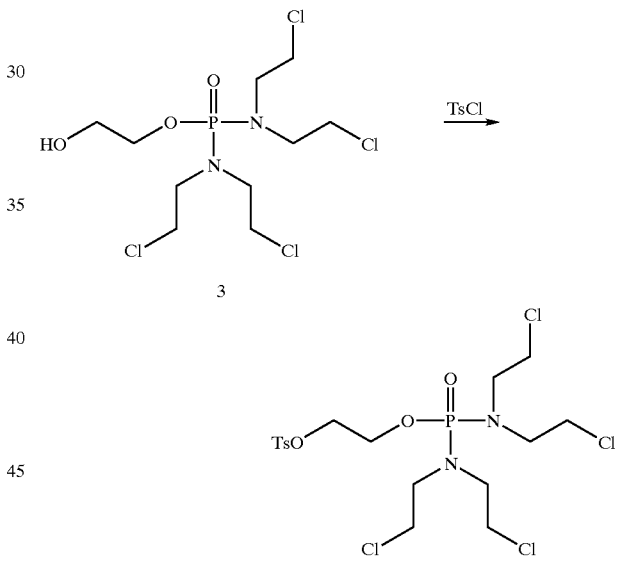

To a solution of compound 3 (0.780 gm, 2 mmol) in THF/H$_2$O (1:1) and 1N NaOH (2 mL) was added a solution of para-toluenesulfonylchloride (0.40 gm, 2.1 mmol) in THF. The reaction mixture was allowed to stir for 24 h at RT. The mixture was diluted with methylene chloride, and washed with 1N HCl. The organic layer was washed with brine, dried over K$_2$CO$_3$ and concentrated to a viscous oil, compound 11 (1.04 gm, 96%)

The table shows compounds that were prepared in a similar fashion

13

[Chemical structure showing phosphoramide compound with R-Q-O-P(=O) core with three N-CH2CH2-X arms]

| Compound | R | Q | X |
|---|---|---|---|
| 12 | Ac | O | Cl |
| 13 | PhCO | O | Cl |
| 14 | PhSO₂ | O | Cl |
| 15 | p-BrPhSO₂ | O | Cl |
| 16 | p-NO₂PhSO₂ | O | Cl |
| 17 | Me | O | Cl |
| 18 | Benzyl | O | Cl |
| 19 | Benzyl | O | Br |
| 20 | p-MePhSO₂ | O | Br |
| 21 | Ac | NH | Cl |
| 22 | PhCO | NH | Cl |
| 23 | p-MePhSO₂ | NH | Cl |

Example 4 Cell Viability

RPMI 8322 human melanoma cells (ATCC) were grown at 37 C in MEM supplemented with 10% fetal bovine serum, 1% L-glutamate, and 0.1% gentamicin. The cells were plated at a density of $2 \times 10^6$ per well in 96-well microtiter plates. Twenty-four hours later, the medium was replaced with the same medium to which test compounds at final concentrations of 1 $\mu$M to 10 mM, and 1% DMSO had been added. The cells were grown in the presence of the compound for an additional 4 days. Each concentration of the compound was tested in triplicate. Cell viability was measured using a standard assay that monitors metabolic conversion of a dye (CellTiter 96™, Promega).

| Compound | $\mu$M to 50% cell viability |
|---|---|
| 3 | 410 |
| 6 | >500 |
| 9 | 490 |
| 15 | >500 |
| 16 | >500 |
| 23 | >500 |

Example 5 Anti-tumor Effects in Mice

Female, 7 weeks old NCr-tu athymic nude mice were purchased from Charles River Laboratories (Raleigh, N.C.) and acclimated in the laboratories one week prior to experimentation. The animals were housed in microisolator cages, at five per cage, in a 12-hour light/dark cycle. The animals received filtered sterilized water and sterile rodent food d lieitum. Animals were observed daily, and clinical signs such as tumor shrinkage were noted.

Tumor Model. Thirty- to forty mg fragments of MX-1 human mammary tumor were implanted subcutaneously in mice near the right axillary area, using a 12-gauge trocar needle and allowed to grow. Tumors were allowed to reach 75–196 mg in weight (75–196 mm³ mm in size) before the start of treatment.

Drug Treatment. Compound 3 was formulated fresh daily at a concentration of 10 mg/mL in 5% ethanol/14% propylene glycol/50% PBS. Compound 3 was administered intraperitoneally for five consecutive days at dosages of 55, 75, and 100 mg/kg/dose. Dosing solutions were administered to mice within 4 hours of formulation. Compounds were administered by exact body weight, with the injection volume being 0.1 mL/10 g body weight.

Tumor measurements. The tumors were measured, and the animals were weighed twice weekly, starting with the first day of treatment. Tumor volume was determined by caliper measurements (mm) and using the formula for an ellipsoid $L \times W^2 / 2 =$ Volume, where L and W refer to the larger and smaller dimensions collected at each measurement. This formula was also used to calculate tumor weight, assuming a unit density (1 mm³=1 mg).

Study duration was 28 days after tumor implantation. Any animal whose tumor reached 4 g in weight was sacrificed prior to study termination.

| Dose (mg/Kg) | Non-Specific Deaths | Tumor Regression Partial | Tumor Regression Complete | Tumor-Free | Days to Doubling |
|---|---|---|---|---|---|
| 100 | 0/8 | 0 | 0 | 0/8 | 7.7 |
| 75 | 0/8 | 0 | 0 | 0/8 | 8.1 |
| 55 | 0/8 | 0 | 0 | 0/8 | 7.2 |
| PBS control | | | | 0/8 | 6.6 |

What is claimed is:
1. A compound of the formula:

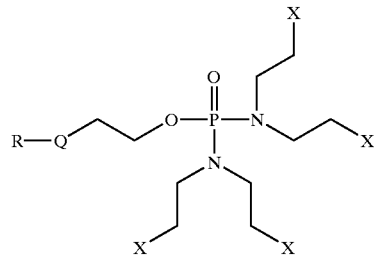

where:
X is a halogen atom;
Q is O, S, or NH; and
R is hydrogen, lower alkyl, substituted lower alkyl, aryl, substituted aryl, heteroaryl, or substituted heteroaryl, or is R'CO—, R'NHCO—, R'SO₂—, or R'NHSO₂—, where R' is hydrogen, lower alkyl, substituted lower alkyl, aryl, substituted aryl heteroaryl, or substituted heteroaryl; or R-Q together is chlorine,
wherein:
said "substituted lower alkyl" group is a lower alkyl which is mono-, di-, or trisubstituted with a group selected from aryl, $R^1$-substituted aryl, heteroaryl, nitro, cyano, halogen, —OR¹, —SR¹, —C(O)R¹, —OC(O)R¹, —C(O)OR¹, —NR¹₂, —SO₂OR¹, —OSO₂R¹, —SO₂NR¹₂, —NR¹SO₂R¹, —CONR¹₂, or —NR¹C(O)R¹, where each R¹ is, independently, hydrogen, lower alkyl, R²-substituted lower alkyl, aryl, R²-substituted aryl, heteroaryl, hetetoary (lower)alkyl, R²-substituted aryl(lower)alkyl, or aryl (lower)alkyl and each R² is, independently, hydroxy, halogen, lower alkyloxy, cyano, thio, nitro, lower alkyl halo-lower alkyl or amino;

said "substituted aryl" group is an aryl substituted with one to three substituents selected from alkyl, substituted alkyl, halogen, cyano, nitro, $-SR^1$, $-OR^1$, $-C(O)R^1$, $-OC(O)R^1$, $-SO_2OR^1$, $-OSO_2R^1$, $-SO_2NR^1{}_2$, $-NR^1SO_2R^1$, $-C(O)OR^1$, $-NR^1{}_2$, $-CONR^1{}_2$, or $-NR^1C(O)R^1$, where each $R^1$ is, independently, hydrogen, lower alkyl, $R^2$-substituted lower alkyl, aryl, $R^2$-substituted aryl, heteroaryl, heteroaryl(lower)alkyl, aryl(lower)alkyl, or $R^2$-substituted aryl(lower)alkyl and each $R^2$ is, independently, hydroxy, halo, lower alkyloxy, cyano, thio, nitro, lower alkyl, halo-lower alkyl or amino, or any two adjacent substituents on the aryl together form a lower alkylenedioxy; and said "substituted heteroaryl" group is a heteroaryl having from one to three substituents selected from alkyl $R^1$-substituted alkyl, halo, cyano, nitro, $-SR^1$, $-OR^1$, $-C(O)R^1$, $-OC(O)R^1$, $-SO_2OR^1$, $-OSO_2R^1$, $-SO_2NR^1{}_2$, $-NR^1SO_2R^1$, $-C(O)OR^1$, $-NR^1{}_2$, $-CONR^1{}_2$, or $-NR^1C(O)R^1$, where each $R^1$ is independently hydrogen, lower alkyl, $R^2$-substituted lower alkyl, aryl, $R^2$-substituted aryl, heteroaryl, heteroaryl(lower)alkyl, aryl(lower)alkyl, or $R^2$-substituted aryl(lower)alkyl and each $R^2$ is, independently, hydroxy, halo, lower alkyloxy, cyano, thio, nitro, lower alkyl halo-lower alkyl, or amino, or any two adjacent substituents on the heteroaryl together form a lower alkylenedioxy; or a pharmaceutically acceptable salt thereof.

2. A compound of claim 1, where:

Q is O, S, or NH; and

R is hydrogen, lower alkyl, substituted lower alkyl, aryl, substituted aryl, heteroaryl, or substituted heteroaryl, or is R'CO—, R'NHCO—, R'SO₂—, or R'NHSO₂—, where R' is hydrogen, lower alkyl, substituted lower alkyl, aryl, substituted aryl, heteroaryl, or substituted heteroaryl.

3. A compound of claim 2, where X is chlorine or bromine.

4. A compound of claim 3, where X is chlorine.

5. A compound of claim 2, where Q is O.

6. A compound of claim 5, where R is R'CO—, R'NHCO—, R'SO₂—, or R'NHSO₂—, where R' is hydrogen, lower alkyl, substituted lower alkyl, aryl, substituted aryl, heteroaryl, or substituted heteroaryl.

7. A compound of claim 6, where R is acetyl, benzoyl, benzenesulfonyl, para-bromobenzenesulfonyl, para-nitrobenzenesulfonyl, para-toluenesulfonyl, or methanesulfonyl.

8. A compound of claim 5, where R is hydrogen, lower alkyl, substituted lower alkyl, aryl, substituted aryl, heteroaryl, or substituted heteroaryl.

9. The compound of claim 8, where R is hydrogen, methyl, or benzyl.

10. The compound of claim 9 that is 2-hydroxyethyl-N, N,N',N'-tetrakis-(2-chloroethyl)phosphorodiamidate or a pharmaceutically acceptable salt thereof.

11. The compound of claim 2, where Q is NH.

12. A pharmaceutical composition comprising a therapeutically effective amount of a compound of claim 1 and at least one pharmaceutically acceptable carrier.

13. The composition of claim 12 further comprising a pharmacologically active agent selected from the group consisting of antibiotics, antineoplastic agents, tumoricidal agents, and tumoristatic agents.

14. A pharmaceutical composition comprising a therapeutically effective amount of a compound of claim 2 and at least one pharmaceutically acceptable carrier.

15. The composition of claim 14 further comprising a pharmacologically active agent selected from the group consisting of antibiotics, antineoplastic agents, tumoricidal agents, and tumoristatic agents.

16. A pharmaceutical composition comprising a therapeutically effective amount of a compound of claim 10 and at least one pharmaceutically acceptable carrier.

17. The composition of claim 16, further comprising a pharmacologically active agent selected from the group consisting of antibiotics, antineoplastic agents, tumoricidal agents, and tumoristatic agents.

18. A method of treatment for a tumor in a mammal, comprising administering to a mammal in need thereof a therapeutically effective amount of a compound of claim 1.

19. A method of treatment for a tumor in a mammal, comprising administering to a mammal in need thereof a therapeutically effective amount of a compound according to claim 2.

20. A method of treatment for a tumor in a mammal, comprising administering to a mammal in need thereof a therapeutically effective amount of a compound according to claim 10.

* * * * *

UNITED STATES PATENT AND TRADEMARK OFFICE
CERTIFICATE OF CORRECTION

PATENT NO.    : 6,506,739 B1                                                                            Page 1 of 1
DATED        : January 14, 2003
INVENTOR(S)  : Herr et al.

It is certified that error appears in the above-identified patent and that said Letters Patent is hereby corrected as shown below:

<u>Title page,</u>
Below item [22], insert:

--                    Related U.S. Application Data
   Provisional application No. 60/325,746, filed on May 2, 2000. --

<u>Column 1,</u>
Line 9, below the caption "CROSS-REFERENCE TO RELATED APPLICATION" should read:
-- This application claims the priority under 35 USC 119(e) of Provisional Application No. 60/325,746, filed May 2, 2000. --

Signed and Sealed this

Second Day of September, 2003

JAMES E. ROGAN
*Director of the United States Patent and Trademark Office*